United States Patent [19]
Henzler et al.

[11] Patent Number: 6,128,073
[45] Date of Patent: Oct. 3, 2000

[54] DEVICE AND METHOD FOR EXAMINING THE SMOOTHNESS OF A SAMPLE SURFACE

[75] Inventors: Martin Henzler, Garbsen; Ralf Kumpe, Wedemark; Hannes Frischat; Franz-Otto Kopp, both of Hannover, all of Germany

[73] Assignee: Wacker Siltronic Gesellschaft für Halbleitermaterialien AG, Burghausen, Germany

[21] Appl. No.: 09/025,674

[22] Filed: Feb. 18, 1998

[30] Foreign Application Priority Data

Feb. 21, 1997 [DE] Germany .......................... 197 06 973

[51] Int. Cl.[7] .................................................. G01N 21/88
[52] U.S. Cl. ........................ 356/72; 356/371; 356/237.2
[58] Field of Search .................................... 356/371, 446, 356/237.2, 237.3, 237.4, 237.5, 72

[56] References Cited

U.S. PATENT DOCUMENTS

| | | |
|---|---|---|
| 3,790,287 | 2/1974 | Cuthbert et al. . |
| 4,290,698 | 9/1981 | Milana ..................................... 356/371 |
| 4,314,763 | 2/1982 | Steigmeier et al. ..................... 356/237 |
| 4,724,318 | 2/1988 | Binnig ..................................... 250/307 |
| 5,254,207 | 10/1993 | Nishizawa et al. ..................... 350/382 |

OTHER PUBLICATIONS

H. Rothe, A. Vasper, SPIE's Annual Meeting '96, Denver, Aug. 4–9, Proc. SPIE No. 2862–06.

*Primary Examiner*—Richard A. Rosenberger
*Attorney, Agent, or Firm*—Collard & Roe, P.C.

[57] ABSTRACT

A device for examining the smoothness of a sample surface includes a scattered-light instrument for scanning the surface with a focused laser beam and for detecting scattered light which is reflected during the scanning of the surface. There is also an instrument for microscopic examination of prominently light-scattering regions of the surface after they have been identified using the scattered-light instrument. This device has an evacuable sample chamber, in which the sample is placed on a sample holder and which has a transparent window through which the laser beam passes before it strikes the surface of the sample. There is also a method for examining a sample using the device.

9 Claims, 1 Drawing Sheet

DEVICE AND METHOD FOR EXAMINING THE SMOOTHNESS OF A SAMPLE SURFACE

BACKGROUND OF THE INVENTION

1. Field of the Invention

The present invention relates to a device and to a method for examining the smoothness of a sample, in particular for examining the surface of a semiconductor wafer. The invention is particularly suitable for locating and characterizing very small defects. The defects can be detected by the scattering of light which they cause. The term "defects" encompasses both particles adhering to the surface and intrinsic faults in the surface structure.

2. The Prior Art

Using scattered-light measurements, it is possible for relatively large surfaces, for example the surfaces of semiconductor wafers, to be scanned fully in a short time. However, the lateral resolution of this measuring method is fairly poor, and so it is not very suitable for characterizing the defects which are found. For accurately examining the defects which are found, it is better to use a high-resolution microscopic method. During the SPIE Annual Meeting '96 in Denver, a measuring station for examining smooth surfaces was proposed, which was equipped with a scattered-light instrument and an AFM (atomic force microscope) (H. Rothe, A. Kasper, SPIE Annual Meeting '96, Denver, August 4–9, Proc.SPIE No. 2862-06).

SUMMARY OF THE INVENTION

It is an object of the present invention to provide a substantially improved development for a measuring station for examining a smooth surface of a sample, in which a scattered-light instrument is combined with a microscope.

The above object is achieved by the present invention which relates to a device for examining a smooth surface of a sample, comprising a scattered-light instrument for scanning the surface with a focused laser beam and for detecting scattered light which is reflected during the scanning of the surface, and an instrument for microscopic examination of prominently light-scattering regions of the surface after these regions have been identified using the scattered-light instrument, which device has an evacuable sample chamber, in which the sample is placed on a sample holder and which has a transparent window through which the laser beam passes before it strikes the surface of the sample.

The device is best suited for comparative examinations of the effects of preparative alterations to the surface of the sample on surface regions identified as prominent. Surface regions of this type can be found repeatedly with a high degree of accuracy. It is particularly advantageous for in situ examinations of the sample surface to be possible as well. That is to say that the samples can be examined microscopically while a preparative alteration to the sample surface is being carried out. The sample chamber is for this reason correspondingly designed so that preparative treatments of the sample surface can be carried out in it. If the nature of the preparation method precludes the possibility of in situ examinations, then the sample chamber may be divided into a measuring chamber and a preparation chamber, the two parts being connected through an vacuum tight lock. The sample can be transferred through the vacuum tight lock using manipulators without breaking the vacuum. In this case, the microscopic examination of prominent surface regions takes place directly after the sample preparation has been completed.

The present invention also relates to a method for examining a smooth surface of a sample using a scattered-light instrument and an instrument for carrying out a microscopic method, comprising the steps of:

a) placing a sample in an evacuable chamber for the purpose of surface examination;

b) scanning a surface of the sample using a scattered-light instrument and identifying a position of prominently light-scattering regions of the surface;

c) examining the prominently light-scattering regions using an instrument for carrying out a microscopic method;

d) carrying out a preparative alteration to the sample surface in the chamber; and e) carrying out a new microscopic examination according to step c).

In a preferred embodiment, it is possible to carry out steps (d) and (e) simultaneously.

The method of the invention makes it possible to examine the local roughness (root mean square roughness) in the Sub-Angstrom range by measuring the highly laterally resolved scattered-light intensity with high detection sensitivity. The method of the invention further permits direct correlation of these data with the surface topography ascertained by scanning probe microscopy examinations. The examinations can take place entirely in an ultra high vacuum (UHV). The sample surface is scanned with the light spot using a deflecting mirror arranged suitably in the optical path outside the UHV. Thus, only the respectively illuminated surface region of the confocal projection reaches the stationary photo detector.

The device and the method of the invention are preferably used for examining the surfaces of semiconductor wafers, in particular for describing the microroughness of the surfaces and for characterizing the surface defects. The semiconductor wafers which undergo the examination preferably have polished or etched surfaces. Preferred samples include coated semiconductor wafers, for example semiconductor wafers provided with an oxide layer or an epitaxial layer, and hard disks.

The scattered-light instrument which is employed in the device may have scanning equipment which moves the sample. However, use is preferably made of a scattered-light instrument in which the scanning equipment guides the light beam over the sample, which remains at rest. The angle of incidence of the light beam on the sample may be fixed or may be adjustable to different values. The scattered light reflected by the sample may be detected at a fixed angle, or in a fixed angular range or in a variable angular range. One or more detectors may be used for detecting the scattered light. It is possible for each detector to pick up the scattered light at a fixed angle, in a fixed angular range or in a variable angular range. Lastly, it is also possible for the laser beam reflected by the sample, or the deviation of this beam, to be detected and employed to locate surface defects.

The instrument for carrying out a microscopic method is a microscope which is preferably selected from a group which comprises AFMs (Atomic Force Microscopes), STMs (Scanning Tunneling Microscopes), SNOMs (Scanning Near Field Optical Microscopes), NOMs (Near Field Optical Microscopes) and TCAFMs (Threshold Current AFMs) or arbitrary combinations of these examination instruments.

The evacuable sample chamber is preferably designed as a ultra-high vacuum (UHV) chamber. It is particularly preferred if the sample chamber is also suitable as a receptacle for carrying out a sample preparation, or if direct access of the sample to a receptacle of this type is possible through a vacuum lock. Preferred preparation methods include CVD (Chemical Vapor Deposition), APCVD (Atmospheric Pressure CVD), LPCVD (Low Pressure CVD), MOMBE (Metal Organic MBE), MBE (Molecular Beam Epitaxy) and heat treatments and oxidizing and etching treatments taking place through the gas phase. In the UHV chamber, it is thusly possible to carry out a preparative alteration to the sample surface.

BRIEF DESCRIPTION OF THE DRAWINGS

Other objects and features of the present invention will become apparent from the following detailed description considered in connection with the accompanying drawing which discloses one embodiment of the present invention. It should be understood, however, that the drawing is designed for the purpose of illustration only and not as a definition of the limits of the invention.

In the drawing, wherein similar reference characters denote similar elements throughout the single view, the one figure shows a preferred embodiment of the device of the invention in a schematic illustration.

DETAILED DESCRIPTION OF PREFERRED EMBODIMENTS

Figure 1:
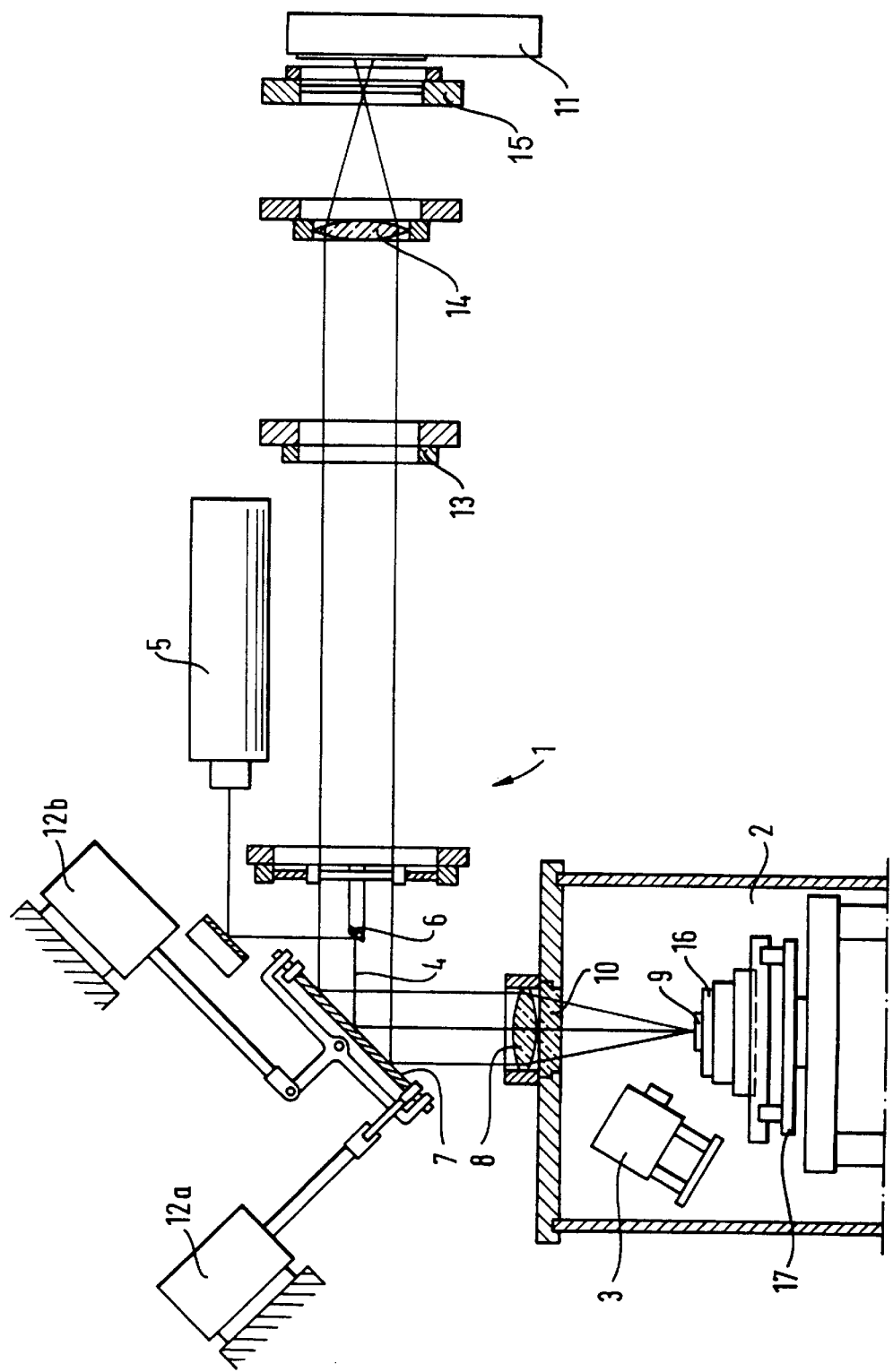

Turning now in detail to the drawing, the device comprises a scattered-light instrument 1 and an STM-type microscope built into an ultra-high vacuum chamber 2. The beam 4 of a laser 5 is focused via an input coupling mirror 6 and a deflecting mirror 7 suspended on gimbals through a lens 8 onto a sample 9 placed on a sample holder 16 in the chamber 2. In this case, the laser beam passes through a transparent window 10 of the chamber. The sample is perpendicular to the optical axis, so that the specularly reflected laser beam is reflected back on itself. The non-specularly scattered light is projected in a solid angle range of preferably 3 to 15° relative to the specularly reflected beam, through the lens 8 in a parallel direction toward a detector 11. Both the center of rotation of the deflecting mirror and the sample are at the focal point of the lens, so that the scattered light strikes the detector irrespective of the position of the deflecting mirror.

The movement of the deflecting mirror, and therefore the function of a scanning instrument, is undertaken by an x- and a y- deflecting unit 12a and 12b which, for example, are based on moving coil systems. In the optical path of the scattered light between the deflecting mirror and the detector, at least a diaphragm 13, a lens 14 and a pin diaphragm 15 are further incorporated. The diaphragm 13 has the purpose of filtering out divergent extraneous radiation. The scattered light arriving at the lens 14 is focused by it onto the pin diaphragm 15 and finally reaches the photo-detector, preferably a photomultiplier. Between the deflecting mirror 7 and the detector 11 is a diaphragm 13, and downstream of the diaphragm 13 is a lens 14. Downstream of the lens 14 is a pin diaphragm 15, and the detector 11 is downstream of the pin diaphragm 15.

A corresponding further improvement in the signal/noise ratio can be achieved by virtue of the confocal focusing in conjunction with the scattered light optical path which extends parallel to the optical axis and is, in principle, arbitrarily extendable. In contrast to the scattered light signal appertaining to the sample surface, noise signals due to defects of window, mirror, and lenses are, in this arrangement, fundamentally divergent and can therefore be filtered out effectively by suitable diaphragms in the optical path.

According to another embodiment, a further diaphragm (not represented in the drawing) may be provided in the optical path of the scattered light, which diaphragm can be used to filter out the scattered light by sectors. It is in this way possible to obtain scattered light data which allow information to be gathered regarding anisotropies of the sample surface which is examined. The driving of the deflecting mirror, the registering of the measured values and the evaluation of the measurement are carried out using a computer (not shown). Light-scattering defects on the surface of the sample cause a scattered light signal to which a specific x,y position is assigned. These prominent regions can subsequently be returned to with a high degree of accuracy and examined more accurately using a microscopic method.

According to the embodiment of the device which is represented, an STM-type microscope is built into the sample chamber. A measuring head 3 belonging to the microscope can be adjusted and driven over the sample using externally operated manipulators (not shown). The sample holder 16 is mounted on x/y/z sliders 17. The sliders can be used to move the sample manually or with computer control into the intended examination position. The sample thus remains in the chamber both during the scattered light measurements and during the microscopic examination. Reactive surfaces thus remain protected from alteration, which would otherwise make it more difficult to interpret the results of the measurement.

On the other hand, the chamber design which also permits sample preparation can be used to alter the surface structure of the sample in a deliberate fashion. The alterations in regions of the surface which were qualified as prominent can be examined once more using the microscopic method either in situ or following the sample preparation.

While several embodiments of the present invention have been shown and described, it is to be understood that many changes and modifications may be made thereunto without departing from the spirit and scope of the invention as defined in the appended claims.

What is claimed is:

1. A device for examining the smoothness of a sample, comprising a scattered-light instrument for scanning a surface of a sample with a focused laser beam and for detecting scattered light which is reflected during the scanning of the surface;

an evacuable sample chamber, in which the sample is placed on a sample holder and said chamber having a transparent window through which the focused laser beam passes before it strikes the surface of the sample; and in said evacuable sample chamber, an instrument for microscopic examination of prominently light-scattering regions of the surface after these regions have been identified using the scattered-light instrument; and wherein said instrument for microscopic examination of the sample is selected from the group consisting of STMs (Scanning Tunneling Microscopes), SNOMs (Scanning Near Field Optical Microscopes), NOMs (Near Field Optical Microscopes) and TCAFMs (Threshold Current AFMs) and the combinations of said examination instruments.

2. The device as claimed in claim 1, comprising a deflecting mirror which is suspended on gimbals in a focal plane of a lens in an optical path of the focused laser beam and by means of which the surface of the sample is scanned.

3. The device as claimed in claim 1, wherein the sample chamber comprises a receptacle for carrying out a method which is selected from a group consisting of CVD (Chemical Vapor Deposition), APCVD (Atmospheric Pressure CVD), LPCVD (Low Pressure CVD), MOMBE (Metal Organic MBE), MBE (Molecular Beam Epitaxy) and heat treatments and oxidizing and etching treatments taking place in the gas phase.

4. A method of examining the smoothness of a sample using a scattered-light instrument and an instrument for carrying out a microscopic method, comprising the steps of:
   a) placing a sample in an evacuable chamber for purpose of surface examination;
   b) scanning a surface of the sample using a scattered-light instrument and identifying a position of prominently light-scattering regions of the surface;
   c) examining the prominently light-scattering regions using an instrument in said evacuable chamber for carrying out a microscopic method; and wherein said instrument for microscopic examination of the sample is selected from the group consisting of STMs (Scanning Tunneling Microscopes), SNOMs (Scanning Near Field Optical Microscopes), NOMs (Near Field Optical Microscopes) and TCAFMs (Threshold Current AFMs) and the combinations of said examination instruments;
   d) carrying out a preparative alteration to the sample surface in the chamber; and
   e) carrying out a new microscopic examination in said evacuable chamber according to step c).

5. The method as claimed in claim 4, wherein steps d) and e) are carried out at the same time.

6. A device for examining the smoothness of a sample, comprising
   a scattered-light instrument for scanning a surface of a sample with a focused laser beam and for detecting scattered light which is reflected during the scanning of the surface;
   an evacuable sample chamber, in which the sample is placed on a sample holder and said chamber having a transparent window through which the focused laser beam passes before it strikes the surface of the sample;
   in said evacuable sample chamber, an instrument for microscopic examination of prominently light-scattering regions of the surface after these regions have been identified using the scattered-light instrument; and wherein said instrument for microscopic examination of the sample is selected from the group consisting of STMs (Scanning Tunneling Microscopes), SNOMs (Scanning Near Field Optical Microscopes), NOMs (Near Field Optical Microscopes) and TCAFMs (Threshold Current AFMs) and the combinations of said examination instruments; and
   a deflecting mirror which is suspended on gimbals in a focal plane of a lens in an optical path of the focused laser beam and by means of which the surface of the sample is scanned with an incident beam;
   so that the incident beam arrives with normal incidence onto the sample for any angular position of the deflecting mirror and that a reflected beam arrives always at the same position of the deflecting mirror.

7. A device for examining the smoothness of a sample, comprising
   a scattered-light instrument for scanning a surface of a sample with a focused laser beam and for detecting scattered light which is reflected during the scanning of the surface;
   an evacuable sample chamber, in which the sample is placed on a sample holder and said chamber having a transparent window through which the focused laser beam passes before it strikes the surface of the sample;
   in said evacuable sample chamber, an instrument for microscopic examination of prominently light-scattering regions of the surface after these regions have been identified using the scattered-light instrument; and wherein said instrument for microscopic examination of the sample is selected from the group consisting of STMs (Scanning Tunneling Microscopes), SNOMs (Scanning Near Field Optical Microscopes), NOMs (Near Field Optical Microscopes) and TCAFMs (Threshold Current AFMs) and the combinations of said examination instruments;
   a deflecting mirror which is suspended on gimbals in a focal plane of a lens in a scanning optical path of the focused laser beam and by means of which the surface of the sample is scanned;
   said deflecting mirror reflecting said scattered light along a reflecting optical path to a detector; and
   between said deflecting mirror and said detector is a diaphragm, and downstream of said diaphragm is a lens, and downstream of said lens is a pin diaphragm and said detector is downstream of said pin diaphragm;
   so that light scattered from lenses, window and mirror, and light from surrounding light sources contribute only a minimum amount to the recorded intensity.

8. A device for examining the smoothness of a sample, comprising
   a scattered-light instrument for scanning a surface of the sample with a focused laser beam and for detecting scattered light which is reflected from the sample surface, said scattered-light instrument comprising
   a laser source emitting the laser beam;
   a detector for detecting the scattered light;
   a deflecting mirror for scanning the laser beam over the sample; and
   a coupling mirror for deflecting the laser beam to the deflecting mirror, said coupling mirror being arranged along an optical axis between the detector and the deflecting mirror, the device further comprising
      an evacuable sample chamber, in which the sample is placed on a sample holder and said chamber having a transparent window through which the focused laser beam passes before it strikes the surface of the sample; and
      in said evacuable sample chamber, an instrument for microscopic examination of prominently light-scattering regions of the surface after these regions have been identified using the scattered-light instrument.

9. A method of examining the smoothness of a sample using a scattered-light instrument and an instrument for carrying out a microscopic method, comprising the steps of
   (a) placing a sample in an evacuable chamber for purpose of surface examination;
   (b) scanning a surface of the sample with a laser beam using the scattered-light instrument comprising placing a coupling mirror along an optical axis between a detector and a deflecting mirror and directing a laser beam to the coupling mirror;
   (c) identifying a position of prominently light-scattering regions of the surface;
   (d) examining the prominently light-scattering regions using an instrument in said evacuable chamber for carrying out a microscopic method;
   (e) carrying out a preparation alteration to the sample surface in the chamber; and
   (f) carrying out a new microscopic examination in said evacuable chamber according to step (d).

* * * * *